(12) United States Patent
Albu (10) Patent No.: US 8,682,446 B2
(45) Date of Patent: Mar. 25, 2014

(54) CONVERTIBLE MONOPOLE AND INVERTED-F ANTENNA ASSEMBLY FOR USE IN A MEDICAL TELEMETRY SYSTEM

(75) Inventor: Ryan Albu, Minneapolis, MN (US)

(73) Assignee: Pacesetter, Inc., Sylmar, CA (US)

( * ) Notice: Subject to any disclaimer, the term of this patent is extended or adjusted under 35 U.S.C. 154(b) by 43 days.

(21) Appl. No.: 13/456,116

(22) Filed: Apr. 25, 2012

(65) Prior Publication Data

US 2013/0053713 A1 Feb. 28, 2013

Related U.S. Application Data

(60) Provisional application No. 61/529,789, filed on Aug. 31, 2011.

(51) Int. Cl.
*A61N 1/08* (2006.01)
(52) U.S. Cl.
USPC .......................................................... 607/60
(58) Field of Classification Search
USPC .......................................................... 607/60
See application file for complete search history.

(56) References Cited

U.S. PATENT DOCUMENTS

| 7,047,076 | B1 | 5/2006 | Li |
| 7,363,087 | B2 | 4/2008 | Nghiem |
| 7,983,760 | B2 * | 7/2011 | Ginggen et al. ................. 607/60 |
| 8,446,326 | B2 * | 5/2013 | Tietjen ........................... 343/757 |

* cited by examiner

*Primary Examiner* — Eric D. Bertram (57) ABSTRACT

An antenna assembly is configured for use with an external device that is configured to wirelessly communicate with an implantable medical device (IMD). The antenna assembly may include an antenna member pivotally secured to a structure through a feed post, and a fixed tail fixed to the structure. The antenna member may be pivotal between a first orientation in which the antenna member electrically connects to the fixed tail, and a second orientation in which the antenna member is disconnected from the fixed tail. The antenna member and the fixed tail cooperatively operate in a first antenna mode when the antenna member is in the first orientation. The antenna member is configured to operate in a second antenna mode when the antenna member is in the second orientation.

13 Claims, 7 Drawing Sheets

CONVERTIBLE MONOPOLE AND INVERTED-F ANTENNA ASSEMBLY FOR USE IN A MEDICAL TELEMETRY SYSTEM

RELATED APPLICATIONS

The present application claims priority to U.S. Provisional Application No. 61/529,789, entitled "Convertible Monopole and Inverted-F Antenna Assembly for Use in a Medical Telemetry System," filed Aug. 31, 2011, which is hereby incorporated by reference in its entirety.

BACKGROUND

Embodiments generally relate to a medical telemetry system, and more particularly to a convertible antenna assembly configured for use with a tablet-based medical telemetry system.

Numerous medical devices exist today, including but not limited to electrocardiographs ("ECGs"), electroencephalographs ("EEGs"), squid magnetometers, implantable pacemakers, implantable cardioverter-defibrillators ("ICDs"), neurostimulators, electrophysiology ("EP") mapping and radio frequency ("RF") ablation systems, and the like (hereafter generally "implantable medical devices" or "IMDs"). IMDs commonly employ one or more leads with electrodes that either receive or deliver voltage, current or other electromagnetic pulses (generally "energy") from or to an organ or tissue (collectively hereafter "tissue") for diagnostic or therapeutic purposes.

Various IMDs are programmed and monitored by an external programmer or external home-based patient care system. For example, a patient may have an IMD that communicates with a base station within the patient's home or a programmer that is used by physicians to change settings within the IMD and/or retrieve data from the IMD. The base station or external programmer device receives data from the IMD about the patient's physiological state. For example, the IMD may transmit stored data or sensed physiological parameters to the base station. Based on the received data, the base station or external programmer device may adjust operating parameters for the IMD.

Conventional external programmers and base stations employ near-field RF data communication techniques that facilitate communication between the IMD and a telemetry wand that is operatively connected to the base station. Typically, the wand of the base station or programmer is placed in close proximity to the IMD in order to establish a communication link. More recently, however, IMD telemetry assemblies have been proposed that employ far-field RF data communication techniques that do not require close proximity between the IMD and the wand of the programmer or base station. Further, some systems do not even include a separate and distinct telemetry wand, and the RF circuitry and antenna are embedded within the housing of the external programmer device or home base station.

Many telemetry systems communicate with IMDs using the Medical Implant Communication Service (MICS) band. Generally, the MICS band is an allocated frequency between 402-405 MHz. The MICS band enables a short-range, wireless link to be maintained between low-power implanted IMDs and an external programmer or base station.

Recently, it has been proposed to size and shape the external programmer device similar to a small notebook computer or tablet (such as an iPad® device offered by Apple). However, difficulties exist in connection with implementing small size external programmers. For example, the RF performance of the telemetry system within the programmer device may be affected as the housing of the programmer becomes smaller and the programmer is portable and handled more frequently by the physician or other user.

As one example of a size-related challenge, it is desirable for a quarter-wave monopole antenna that operates in the 402-405 MHz MICS band, to be about 7" long, and to be mounted above a ground plane within the external programmer. However, physicians and other users may find such an antenna to be obtrusive, distracting, or simply unwieldy. The antenna length and location limit the amount of size reduction that can be achieved in the overall form-factor (size envelope) for the portable, compact tablet-type programmer device or base station.

Additionally, incorporating a monopole antenna within a tablet-type device poses further drawbacks. The embedded antenna exhibits certain tuning characteristics that affect the antenna performance. A user grasping the exterior housing of the tablet-type programmer device may change the tuning characteristics of the antenna and cause the antenna to become detuned. The degree and manner by which the antenna is "detuned" is dependent, at least in part, upon where the user grasps the antenna.

Further, signal attenuation become a greater concern as the programmer size is reduced. Signals that are transmitted in the RF field to/from the antenna of the programmer device may be attenuated by the user, when the user places his/her hands on the housing of the tablet-type programmer. The RF field communications signals may be attenuated by the tablet housing or other conductive materials proximate to the antenna. Miniaturization of the tablet may not provide enough space for a properly-sized conventional antenna assembly and may cause the conventional antenna assembly to be inadequately shielded from the electronics on a motherboard of the tablet programmer device.

Also, with portability, the user may hold the tablet programmer in various positions and orientations with respect to the patient while in use. As the table programmer is moved or re-oriented, the polarization between the tablet antenna and the IMD antenna may become mismatched. Further, there may be nulls in the transmission/reception pattern generated by conventional antenna assemblies, such that the when the IMD is located in a null, a communications link cannot be maintained between the IMD and the programmer device.

SUMMARY

In accordance with embodiments described herein, methods, systems and assemblies are described that address the above discussed problems.

Certain embodiments provide an antenna assembly that is configured for use with an external device that is configured to wirelessly communicate with an implantable medical device (IMD). The antenna assembly may include an antenna member pivotally secured to a structure through a feed post, and a fixed tail fixed to the structure. The antenna member may be pivotal between a first orientation in which the antenna member electrically connects to the fixed tail, and a second orientation in which the antenna member is disconnected from the fixed tail. The antenna member and the fixed tail cooperatively operate in a first antenna mode when the antenna member is in the first orientation. The antenna member is configured to operate in a second antenna mode when the antenna member is in the second orientation.

The first antenna mode may be an inverted-F antenna mode. The second antenna mode may be a monopole antenna mode.

The antenna member may include a free end and a pivot end. The pivot end may be proximate the feed post. The fixed tail may connect to the antenna member proximate the pivot end in the first orientation.

The fixed tail may include a fixed post integrally connected to an extension beam configured to connect to the antenna member in the first orientation. The fixed tail may be securely fixed to a side of the structure.

The antenna member and the fixed tail may form a linear antenna arm in the first orientation. The antenna member, in the second orientation, may be perpendicular to a planar surface of the structure.

The structure may include, or be incorporated into, an electronic tablet. The structure may be a ground plane of the electronic tablet, for example.

The antenna member may be formed on a printed circuit board. The antenna member may form a meandering path on the printed circuit board. The meandering path may be regular and repeating. The meandering path may include linear portions. The meandering path may include arcuate portions.

Certain embodiments provide a method of converting a single antenna assembly between different antenna orientations. The method may include positioning the single antenna assembly connected to a structure in a first antenna orientation, and pivoting at least a portion of the single antenna assembly relative to the structure into a second antenna orientation.

The positioning may include positioning the single antenna assembly in one of an inverted-F orientation or monopole orientation. The pivoting may include pivoting the portion of the single antenna assembly relative to the structure into one of a monopole orientation or an inverted-F orientation.

The method may include incorporating the structure into an electronic tablet. The method may include forming at least a part of the single antenna assembly on a printed circuit board.

DETAILED DESCRIPTION

Figure 1:
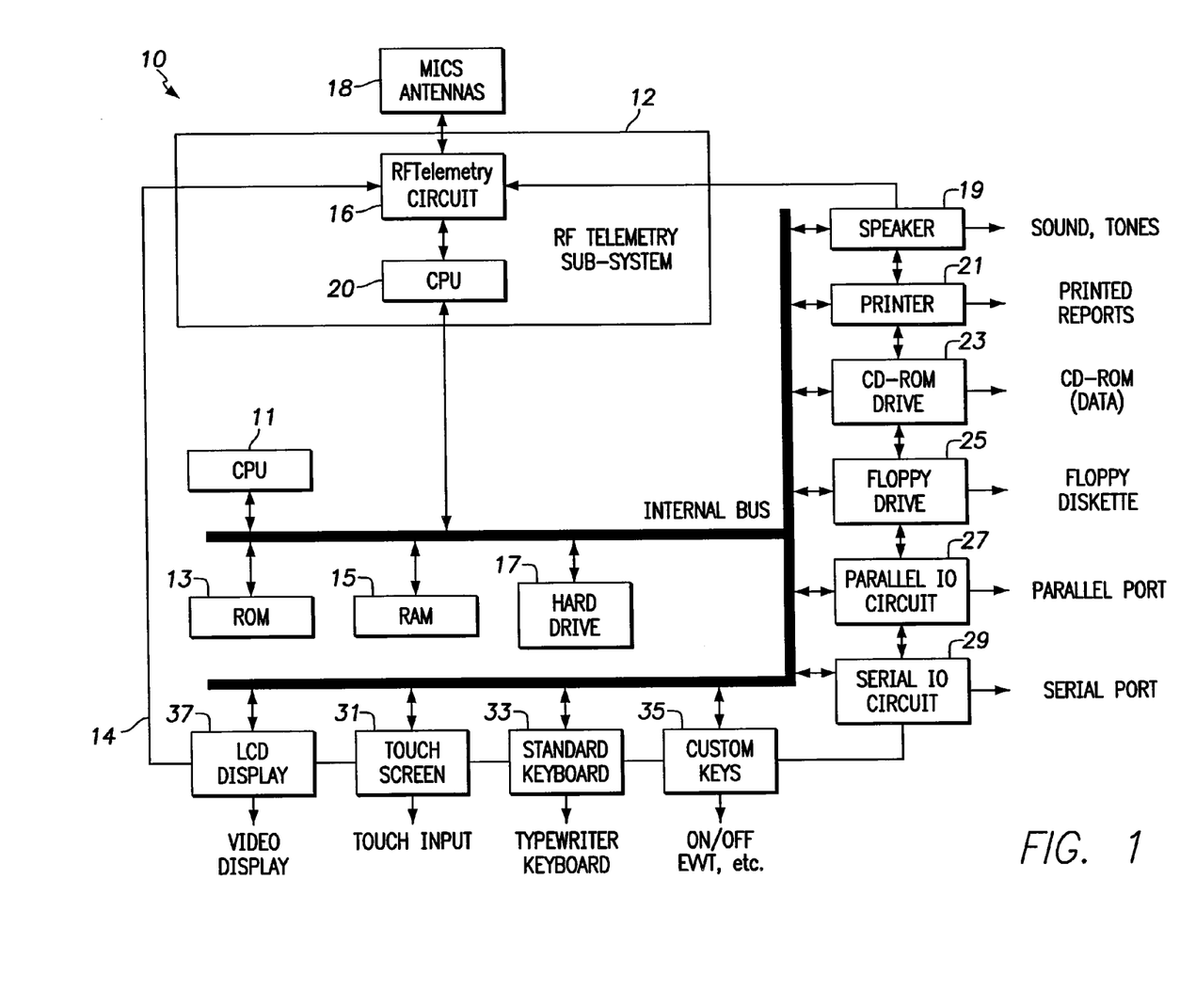
FIG. 1 illustrates a functional block diagram of an external device, formed according to an embodiment.

FIG. 1 illustrates a functional block diagram of an external device 10, formed according to an embodiment. The external device 10 may represent a handheld portable tablet-type programmer device used by physicians and others to communicate with, collect data from, program and reprogram, an IMD. Alternatively, the external device 10 may be a cell phone, personal computer, or laptop computer. Additionally, the external device 10 may be a standalone antenna assembly. Optionally, the external device 10 may be a patient care system, such as the Merlin® home patient care system offered by St. Jude Medical. The external device 10 may include an RF telemetry subsystem 12 that communicates with an implantable medical device (IMD) and/or a network 14. The telemetry subsystem 12 includes an RF telemetry circuit 16 operatively connected to one or more MICS antennas 18. The telemetry circuit 16 is also operatively connected to a controller or processing unit 20.

The external device 10 may be a workstation, a portable computer, an IMD programmer, a PDA, a cell phone and the like. The external device 10 may include an internal bus that connects/interfaces with a Central Processing Unit (CPU) 11, ROM 13, RAM 15, a hard drive 17, speaker 19, a printer 21, a CD-ROM drive 23, a floppy drive 25, a parallel I/O circuit 27, a serial I/O circuit 29, a display 37, a touch screen 31, a standard keyboard connection 33, custom keys 35, and the RF telemetry subsystem 12. The internal bus may include an address/data bus that transfers information between the various components described herein. The hard drive 17 may store operational programs as well as data, such as waveform templates and detection thresholds.

The CPU 11 may include a microprocessor, a micro-controller, or equivalent control circuitry, designed specifically to control interfacing with the external device 10 and with the IMD or network 14. The CPU 11 may include RAM or ROM memory, logic and timing circuitry, state machine circuitry, and I/O circuitry to interface with the IMD. The touch screen 31 may display graphic information relating to the IMD and/or the network 14. The touch screen 31 is configured to accept a user's touch input when selections are made. The keyboard 33 (for example, a "QWERTY" typewriter keyboard) is configured to allow a user to enter data into the displayed fields, as well as interface with the RF telemetry subsystem 12. Further, the custom keys 35 are configured to selectively turn on/off (for example, EVVI) the external device 10. The printer 21 is configured to print copies of reports for a physician to review or to be placed in a patient file, and the speaker 19 is configured to provide an audible warning (for example, sounds and tones) to the user. The parallel I/O circuit 27 interfaces with a parallel port The serial I/O circuit 29 interfaces with a serial port. The floppy drive 25 is configured to accept diskettes, for example. Optionally, the floppy drive 25 may be a USB port or other interface capable of communicating with a USB device such as a memory stick. The CD-ROM drive 23 accepts CD ROMs.

As noted above, the RF telemetry subsystem 12 includes the central processing unit (CPU) 20 in electrical communication with the RF telemetry circuit 16. The telemetry circuit 16 may be connected to implantable leads to receive and process cardiac signals. Optionally, the cardiac signals sensed by the leads may be collected by an IMD and then wirelessly transmitted to the telemetry subsystem 12 of the external device 10.

The telemetry circuit 16 may be operatively connected to, and/or in communication with, a telemetry wand. The external device 10 may wirelessly communicate with the IMD and utilize protocols, such as Bluetooth, GSM, infrared wireless LANs, HIPERLAN, 3G, satellite, as well as circuit and packet data protocols, and the like. Alternatively, a hard-wired connection may be used to connect the external device 10 to the IMD.

Figure 2:
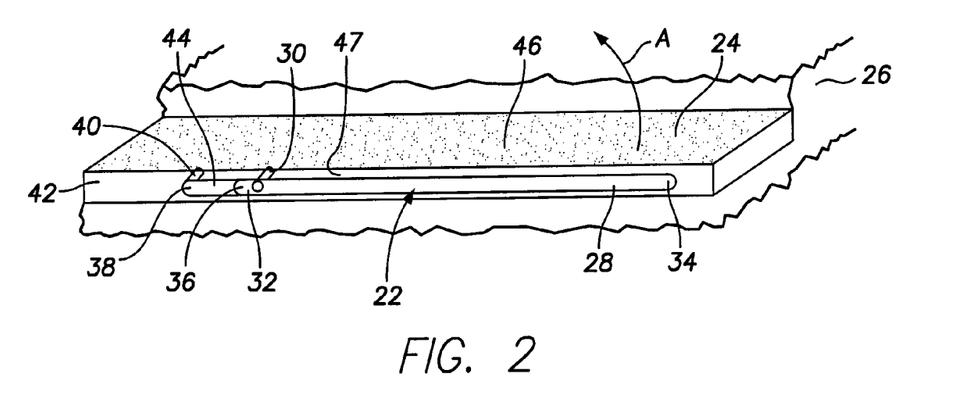
FIG. 2 illustrates an isometric view of an antenna assembly in an inverted-F orientation, according to an embodiment.

FIG. 2 illustrates an isometric view of an antenna assembly 22 in an inverted-F orientation, according to an embodiment. In the inverted-F orientation, the antenna assembly 22 is configured to operate in an inverted-F antenna mode (that is, as an inverted-F antenna). The antenna assembly 22 is operatively connected to a structure, such as a planar member, layer, block, wall, or the like. For example, the antenna assembly 22 may be connected to a ground plane 24 within a tablet 26, for example. The antenna assembly 22 includes a conductive, rod-shaped antenna member 28 that pivotally connects to the ground plane 24 through an antenna feed post 30. As shown, the feed post 30 extends through a pivot end 32 of the antenna member 28. The pivot end 32 is distally located from a free end 34 of the antenna member 28.

A contacting extension 36 of the antenna member 28 extends past the feed post 30 toward a fixed tail 38. The fixed tail 38 includes a fixed post 40 that is fixedly secured into the edge or side 42 of the ground plane 24. The fixed tail 38 extends along and lies within a common plane with the ground plane 24. The fixed post 40 integrally connects to an extension beam 44 that contacts the contacting extension 36 of the antenna member 28.

As shown in FIG. 2, the antenna assembly 22 may extend from the side 42 of the ground plane. The surface of the side 42 is perpendicular to a planar upper surface 46 of the ground plane 24. The feed post 30 and the fixed post 40 locate the antenna member 28 and the extension beam 44, respectively, a distance away from the side 42. A clearance gap 47 is formed between the side 42 of the ground plane 24 and each of the antenna member 28 and the extension beam 44.

As shown in FIG. 2, the antenna member 28 and the extension beam 44 of the fixed tail 38 are aligned in the inverted-F orientation. That is, the extension beam 44 contacts the contacting extension 36 of the antenna member 28 in the inverted-F orientation to generally form an unbroken linear connection between the antenna member 28 and the fixed tail 38. In this configuration, the antenna assembly 22 operates as an inverted-F antenna.

Figure 3:
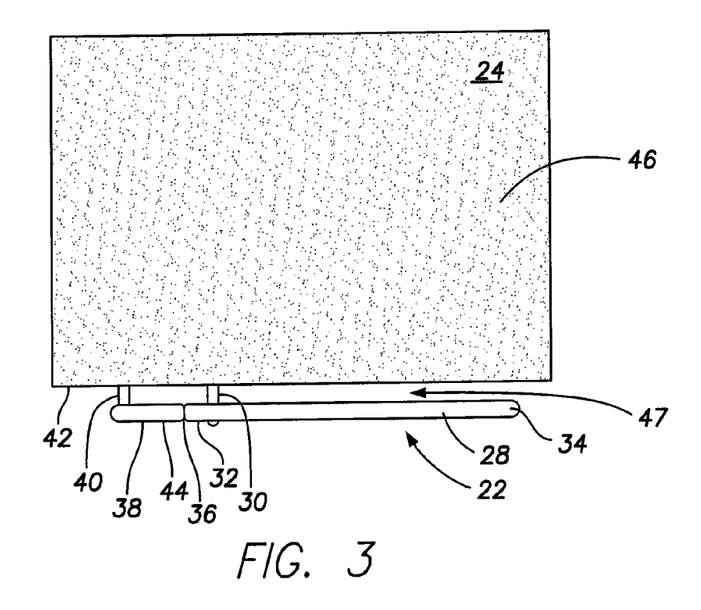
FIG. 3 illustrates a top plan view of an antenna assembly in an inverted-F orientation, according to an embodiment.

FIG. 3 illustrates a top plan view of the antenna assembly 22 in the inverted-F orientation. An inverted F-antenna, such as the antenna assembly 22 shown in FIGS. 2 and 3, is an aperture antenna. The feed from the ground plane 24 for the antenna assembly 22 is the feed post 30. In this orientation, the antenna member 28 and the extension beam 44 connect to form an arm of the antenna assembly 22. The arm may have a length that is roughly a quarter of a wavelength. The fixed post 40 of the fixed tail 38 is shorted to the ground plane 24. As shown, the feed post 30 is closer to the fixed tail 38 than to the free end 34 of the antenna member 28.

The polarization of the antenna assembly 22 may be vertical, and the radiation pattern may be roughly donut shaped, with the axis of the donut in the vertical direction. As shown in FIGS. 2 and 3, the structure of the antenna assembly 22 in this particular configuration resembles an inverted F.

The antenna assembly 22 may be converted from the inverted F orientation shown in FIGS. 2 and 3, to a monopole orientation. In order to convert the antenna assembly 22, a user grasps the free end 34 of the antenna member 28 and pivots the antenna member 28 upwardly about the feed post 30 in the direction of arc A (shown in FIG. 2). In doing so, the contacting extension 36 of the antenna member 28 breaks contact with the extension beam 44 of the fixed tail 38, thereby changing the antenna assembly 22 from an inverted F antenna to a monopole antenna.

Figure 4:
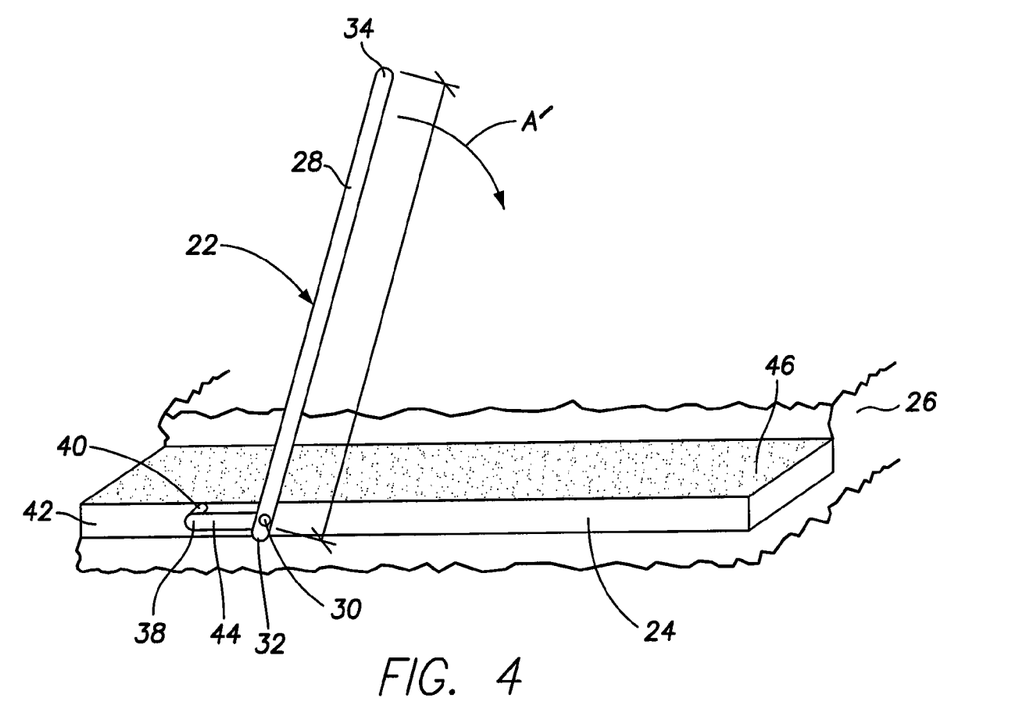
FIG. 4 illustrates an isometric view of an antenna assembly in a monopole orientation, according to an embodiment.
Figure 5:
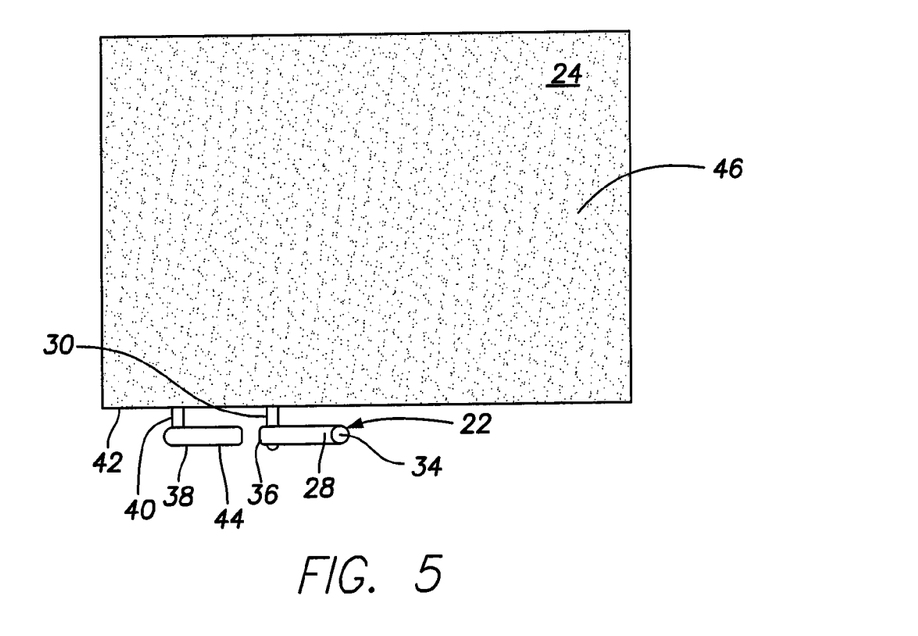
FIG. 5 illustrates a top plan view of an antenna assembly in a monopole orientation, according to an embodiment.

FIG. 4 illustrates an isometric view of the antenna assembly 22 in a monopole orientation, according to an embodiment. FIG. 5 illustrates a top plan view of the antenna assembly 22 in the monopole orientation. In the monopole orientation, the antenna assembly 22 is configured to operate in monopole antenna mode (that is, as a monopole antenna).

Referring to FIGS. 4 and 5, in the monopole orientation, the antenna member 28 has been pivoted upwardly about a longitudinal pivot axis of the feed post 30. Accordingly, the contacting extension 36 of the antenna member 28 no longer contacts the extension beam 44 of the fixed tail 38.

In contrast to the inverted-F orientation, the polarization of the antenna assembly 22 in the monopole orientation may be orthogonal to the inverted-F orientation. Therefore, in changing between inverted-F to monopole orientations, the embodiments provide an adaptable antenna assembly 22. The antenna assembly 22 may be constructed as a multi-segment antenna including the antenna member 28 and the extension beam 44. When the antenna member 28 and extension beam 44 are aligned along a common longitudinal axis, the antenna member 28 and the extension beam 44 electrically join with one another to form a single composite antenna. When the antenna member 28 and extension beam 44 are oriented at a non-parallel angle to one another, the antenna member 28 and the extension beams are electrically disconnected from one another such that the antenna member 28 forms a separate antenna distinct from the extension beam 44.

Referring to FIG. 4, in particular, in order to convert the antenna assembly 22 back to the inverted-F orientation, a user grasps the free end 34 of the antenna member 28 and pivots the antenna member 28 back down in the direction of arc A', until the contacting extension 36 contacts the extension beam 44 of the fixed tail 38, thereby forming a linear arm between the antenna member 28 and the extension beam 44.

Referring to FIGS. 2-5, the antenna assembly 22 provides an antenna member 28 that is positioned to the side of the ground plate 24, and therefore the tablet 26, for example, that includes the ground plate 24. The antenna member 28 may be flipped up with respect to the side of the tablet 26 (such that a user does not simultaneously contact the tablet 26 and the antenna assembly 22), thereby preventing hand-detuning of the antenna assembly 22 by a user. As noted, the flipped-up antenna assembly 22 provides a monopole orientation, while the flipped-down, linearly-connected antenna assembly provides an inverted-F orientation.

In order to maintain connection between the contacting extension 36 of the antenna member 28 and the extension beam 44 of the fixed tail 38 in the inverted-F orientation, one or both of the antenna member 28 and the extension beam 44 may be spring-biased, in order to maintain adequate connection between the two components. Alternatively, the contacting extension 36 and the extension beam 44 may latchably, snapably, or otherwise removably engage one another so that they provide a selective, robust electrical connection therebetween.

Figure 8A:
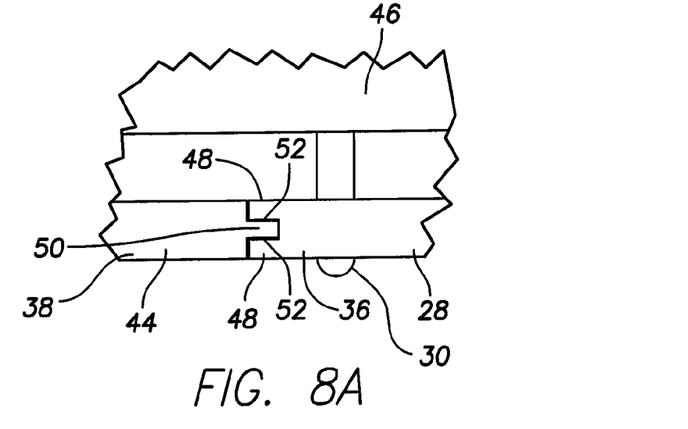
FIG. 8a illustrates a top view of a connection interface between a contacting extension of an antenna member and an extension beam of a fixed tail, according to an embodiment.

FIG. 8a illustrates a top view of a connection interface between the contacting extension 36 of the antenna member 28 and the extension beam 44 of the fixed tail 38, according to an embodiment. As shown, the contacting extension 36 may include opposed prongs 48 that receive and retain an outwardly extending barb 50 of the extension beam 44. Optionally, the extension beam 44 may include the prongs, while the contacting extension 36 includes the barb.

The prongs 48 may include protuberances, bumps, detents, or the like 52 and/or the barb 50 may include outwardly-directed protuberances, bumps, detents, or the like 52. The detents 52 are configured to securely mate with reciprocal members, such as indents, formed in the other of the prongs 48 or the barb 50.

When the contacting extension 36 mates with the extension beam 44, the detents 52 deflect laterally to provide a robust, secure, conductive connection between the antenna member 28 and the fixed tail 38. The connection between the contacting extension 36 and the extension beam 44 may include a spring-biased fit or connection, a pressure fit or connection, an interference fit or connection, or any other such configuration that provides a reliable conductive connection between the two components.

Figure 8B:
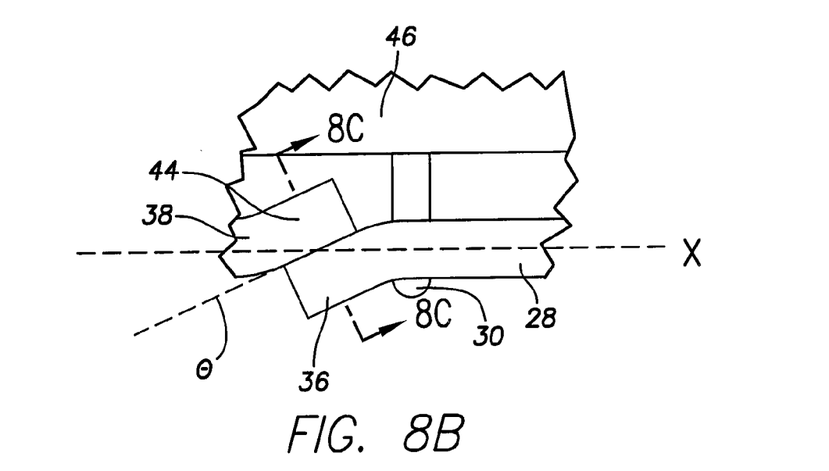
FIG. 8b illustrates a top view of a connection interface between a contacting extension of an antenna member and an extension beam of a fixed tail, according to an embodiment.

FIG. 8b illustrates a top view of a connection interface between the contacting extension 36 of the antenna member 28 and the extension beam 44 of the fixed tail 38, according to an embodiment. In this embodiment, upon connection, the contacting extension 36 and the extension beam 44 deflect from their longitudinal axes x at an angle θ. As shown, the contacting extension 36 deflects in one direction, while the extension beam 44 deflects in the opposite direction (note, the deflection is exaggerated in FIG. 8b in order to clearly show the deflection). Thus, upon connection, the extension beam 44 and the contacting extension 36 may be slightly offset from one another. The offset, deflecting relationship facilitates a frictional conductive interface, as the extension beam 44 and the contacting extension 36 exert equal, but opposite, deflective forces into each other.

Figure 8C:
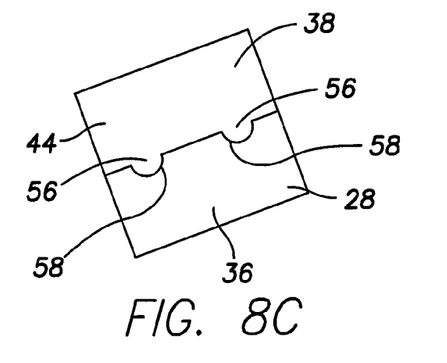
FIG. 8c illustrates a cross-sectional view of a connection interface through line 8c-8c of FIG. 8b, according to an embodiment.

FIG. 8c illustrates a cross-sectional view of a connection interface through line 8c-8c of FIG. 8b. As shown, the extension beam 44 may include outwardly protruding protuberances 56, such as bumps, posts, studs, nubs, or the like that are received and frictionally retained by recessed members 58, such as cavities, recesses, indents, or the like, formed in the contacting extension 36. Alternatively, the extension beam 44 may include the recessed members, while the contacting extension 36 includes the protuberances. The protuberances 56 and recessed members 58 further facilitate the frictional conductive interface between the contacting extension 36 and the fixed tail 38.

Figure 6:
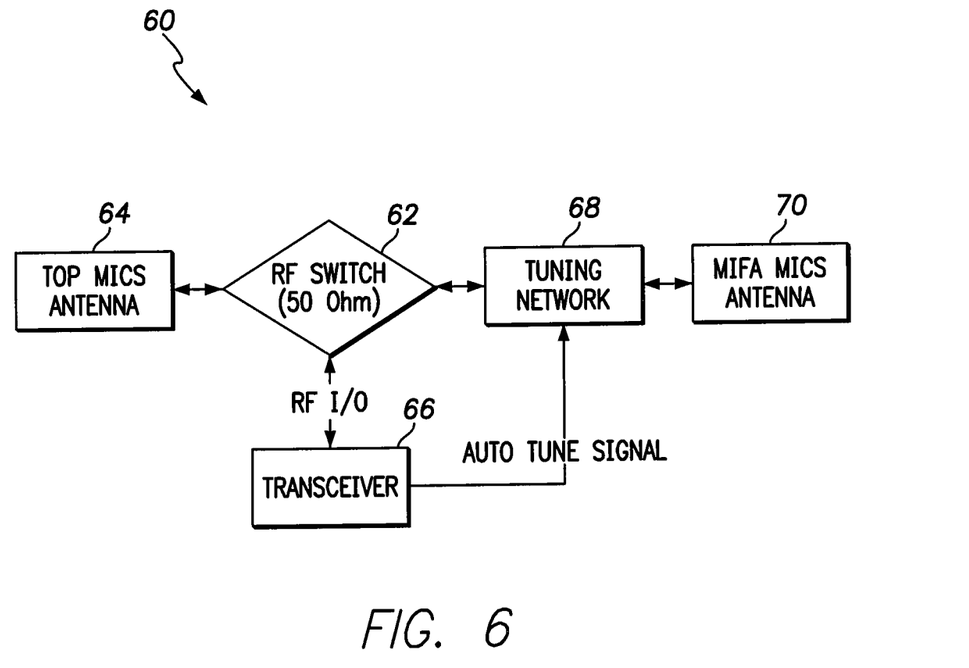
FIG. 6 illustrates a block diagram of a telemetry subsystem, according to an embodiment.

FIG. 6 illustrates a block diagram of a telemetry subsystem 60, according to an embodiment. The telemetry subsystem 60 may include an RF switch 62 electrically connected to a top MICS antenna 64. The RF switch 62 may also be electrically connected to a transceiver 66 and a tuning network 68. The tuning network 68 may, in turn, be electrically connected to a monopole/inverted F antenna (MIFA) antenna assembly 70, such as a MICS antenna assembly, such as the antenna assembly 22 described above.

The tuning network 68 may include a radio operatively connected to a processing unit and a display. The tuning network 68 is configured to operate to provide user feedback on the display to adjust antenna position, as described below. In order to tune, the tuning network 68 acts to adjust an impedance to a select band.

Figure 7:
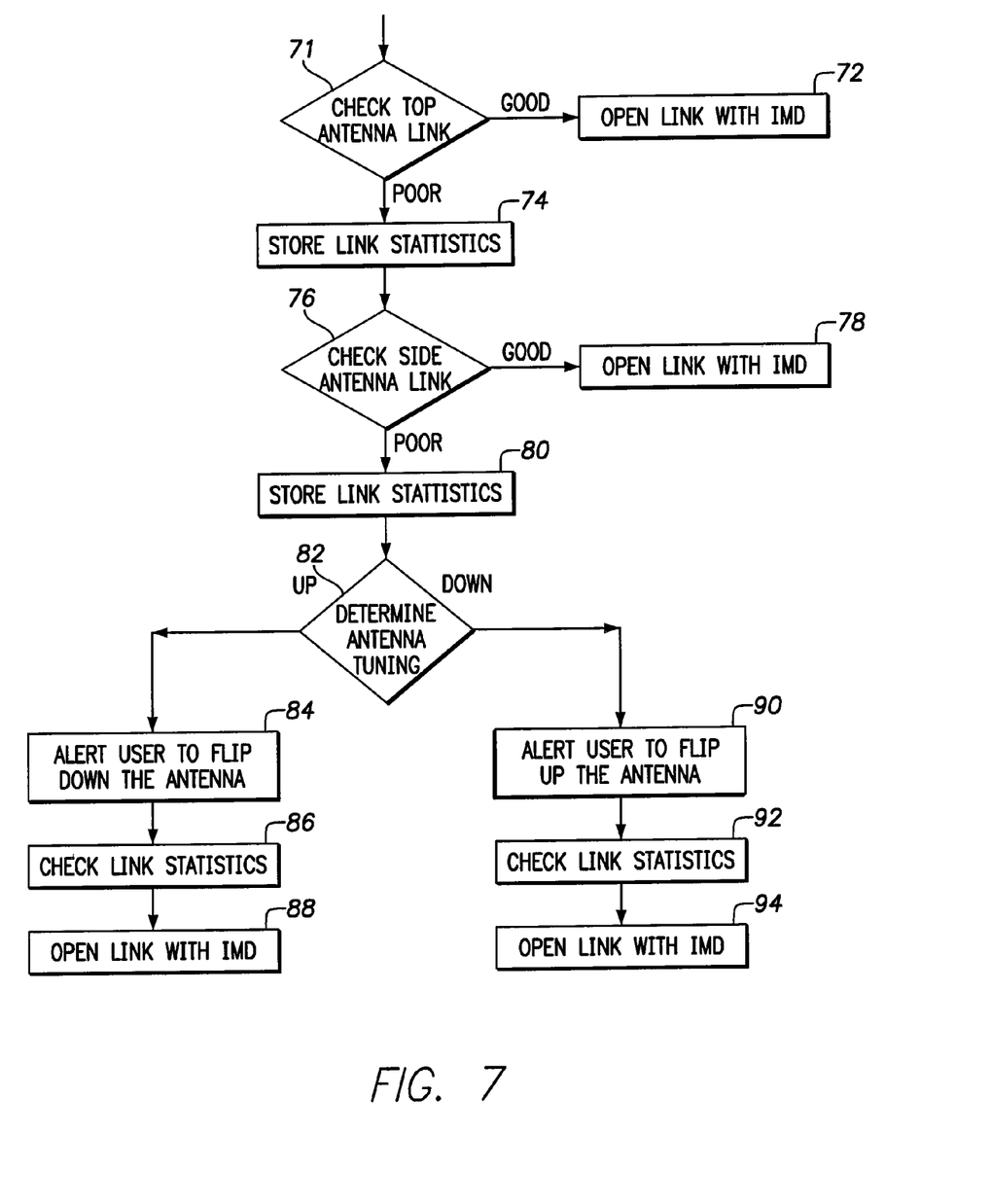
FIG. 7 illustrates a flow chart of a method of operating a telemetry system, according to an embodiment.

FIG. 7 illustrates a flow chart of a method of operating a telemetry system, according to an embodiment. At 71, a top MICS antenna link of a telemetry subsystem is checked. If the link is good, then a link with an IMD is opened at 72. If, however, the link is poor, then link statistics are stored at 74.

After storing the link statistics, at 76, a side antenna (such as a MIFA MICS antenna) link is checked. If the link is good, then at 78, the link is opened with the IMD. If, however, the link is poor, then the link statistics are stored at 80.

After storing the link statistics at 80 due to poor top and bottom antenna links, the antenna tuning is determined at 82. If the antenna is up, the user is alerted at a computer station to flip down the antenna at 84. The link statistics are then checked at 86, and the link is opened with the IMD at 88.

If, however, the link is down, the user is alerted at 90 to flip the antenna up at 90. The link statistics are then checked at 92, and the link with the IMD is opened at 94.

The steps of the process shown and described with respect to FIG. 7 may be performed in conjunction with a computer device, system, and/or network, such as that shown in FIG. 1, for example.

Embodiments provide a convertible antenna assembly that allows a user to select and convert between different antenna modes. The antenna assembly may be selectively converted between an inverted-F antenna mode, and a monopole mode. However, various other antenna configurations and modes may be used. For example, the antenna assembly may be converted between an inverted-F antenna configuration to a folded dipole configuration. Optionally, the antenna assembly may be a dipole antenna when flipped down, and a monopole antenna when flipped up.

Thus, embodiments provide a convertible antenna assembly that allows a user to select and convert between an inverted-F antenna orientation and a monopole antenna orientation. Embodiments provide antenna selective polarization and pattern diversity. Unlike prior antenna systems, embodiments are less susceptible to hand-detuning or attenuation.

Optionally, the antenna assembly may include one or more flip monopole antennas in addition to a fixed inverted-F antenna. For example, a fixed inverted-F antenna may be on the side of the tablet, while a flip monopole antenna may be on top of the tablet. An additional flip monopole antenna may be on the side of the tablet as well. Moreover, in addition to the convertible assembly shown in FIG. 2-5, an additional dedicated monopole flip antenna may be positioned on an opposite side of the tablet, for example.

The antenna may be a metal rod, flat metal strip, helical coil, or may be various other configurations on a printed circuit board, such as a meanderline trace.

Figure 9:
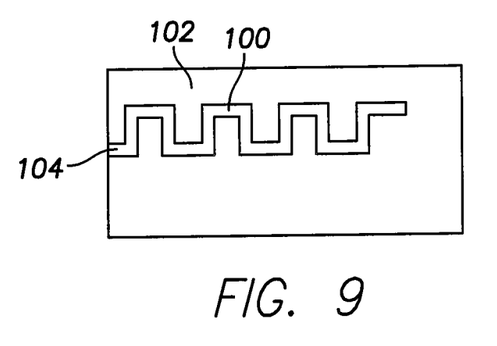
FIG. 9 illustrates a top view of an antenna member on a printed circuit board, according to an embodiment.

FIG. 9 illustrates a top view of an antenna member 100 on a printed circuit board 102, according to an embodiment. The antenna member 100 may form a meandering path on the printed circuit board 102. The meandering path allows the antenna member 100 to have sufficient length for a monopole configuration, while compacting the size onto the printed circuit board. A connection end 104 of the antenna member 100 may connect to the fixed tail 38 (shown in FIG. 2, for example), as discussed above. As shown, the antenna member 100 includes a regular, repeating pattern of turns. Alternatively, the turns may be irregular and non-repeating. Optionally, the printed circuit board 102 may be on or within a tablet, as opposed to being a flappable antenna member.

Figure 10:
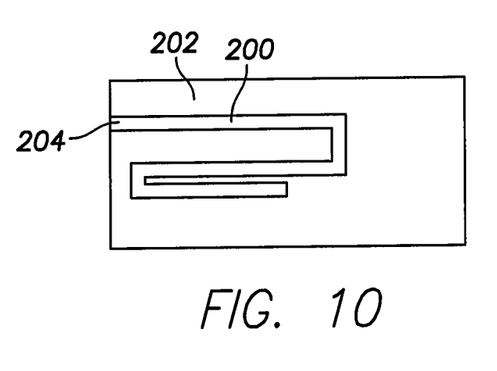
FIG. 10 illustrates a top view of an antenna member on a printed circuit board, according to an embodiment.

FIG. 10 illustrates a top view of an antenna member 200 on the printed circuit board 202, according to an embodiment. A connection end 204 of the antenna member 200 may connect to the fixed tail 38 (shown in FIG. 2, for example), as discussed above. In this embodiment, the antenna member 200 does not include a repeating pattern of turns. Instead, the meandering path is asymmetrical, irregular, and varied. Various patterns may be used. For example, instead of linear portions, the antenna member 200 may include arcuate, curved portions. The antenna member 200 may include arcuate, semi-circular turns. Additionally, the antenna member 200 may include linear turns and arcuate turns. Moreover, the antenna member 200 may be a coiled antenna member having expanding winding portions about a center.

Figure 11:
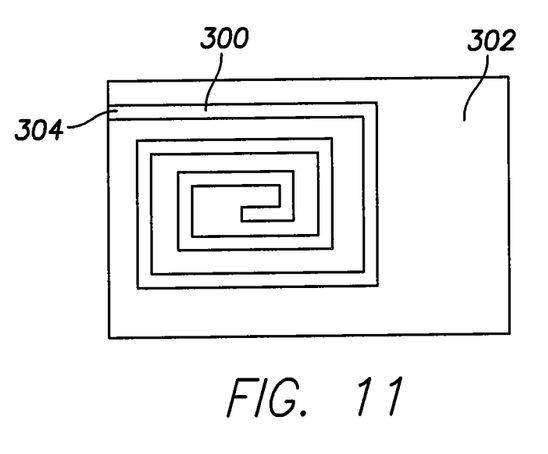
FIG. 11 illustrates a top view of an antenna member on a printed circuit board, according to an embodiment.

FIG. 11 illustrates a top view of an antenna member 300 on a printed circuit board 302, according to an embodiment. A connection end 304 of the antenna member 300 may connect to the fixed tail 38 (shown in FIG. 2, for example), as discussed above. In this embodiment, the meandering path resembles a spiral. The spiral may have straight, linear portions that connect to other straight linear portions, at right angles, for example. Alternatively, the spiral may have semi-circular arcuate portions that wind about a center of the spiral.

Notably, various other meandering paths may be used, as well. For example, an antenna member may include zig-zag portions that extend over a printed circuit board. The antenna member may resemble various shapes, such as a square, rectangle, triangle, or the like, on a printed circuit board. As noted above, the antenna member may form a regular, repeating shape, or may be irregular and non-repeating. In short, the antenna member may be sized and shaped to maximize overall length on a limited space of a printed circuit board, for example.

Additionally, the antenna member may be various other types of antennas. For example, the antenna member may be a helical antenna, a loop antenna, a dipole antenna, or the like.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. An antenna assembly configured for use with an external device that is configured to wirelessly communicate with an implantable medical device (IMD), the antenna assembly comprising:
    an antenna member pivotally secured to a structure through a feed post; and
    a fixed tail fixed to the structure, wherein the antenna member is pivotal between a first orientation in which the antenna member electrically connects to the fixed tail, and a second orientation in which the antenna member is disconnected from the fixed tail,
    wherein the antenna member and the fixed tail cooperatively operate in a first antenna mode when the antenna member is in the first orientation, and wherein the antenna member is configured to operate in a second antenna mode when the antenna member is in the second orientation.

2. The antenna assembly of claim 1, wherein the first antenna mode is an inverted-F antenna mode.

3. The antenna assembly of claim 1, wherein the antenna member comprises a free end and a pivot end, wherein the pivot end is proximate the feed post, and wherein the fixed tail connects to the antenna member proximate the pivot end in the first orientation.

4. The antenna assembly of claim 1, wherein the fixed tail comprises a fixed post integrally connected to an extension beam configured to connect to the antenna member in the first orientation, wherein the fixed tail is securely fixed to a side of the structure.

5. The antenna assembly of claim 1, wherein the antenna member and the fixed tail form a linear antenna arm in the first orientation.

6. The antenna assembly of claim 1, wherein the antenna member, in the second orientation, is perpendicular to a planar surface of the structure.

7. The antenna assembly of claim 1, wherein the second antenna mode is a monopole antenna mode.

8. The antenna assembly of claim 1, wherein the antenna member is formed on a printed circuit board.

9. The antenna assembly of claim 8, wherein the antenna member forms a meandering path on the printed circuit board.

10. The antenna assembly of claim 9, wherein the meandering path is regular and repeating.

11. The antenna assembly of claim 9, wherein the meandering path comprises linear portions.

12. The antenna assembly of claim 9, wherein the meandering path comprises arcuate portions.

13. The antenna assembly of claim 1, wherein the structure comprises a ground plane.

* * * * *